United States Patent [19]

Bonal de Falgas et al.

[11] Patent Number: 5,985,937
[45] Date of Patent: Nov. 16, 1999

[54] USE OF 2,4-DISTRIBUTED PHENOL DERIVATIVES AS 5-LIPOXYGENASE INHIBITORS

[75] Inventors: Joaquin Bonal de Falgas, Barcelona; Lorenzo Lopez Belmonte, Cercedilla; Luis Vila Navarro, Barcelona; Antonio Maria Molins Pujol, Manresa; Luis Lacoma Novales, Barcelona, all of Spain

[73] Assignee: Bobel 246 S.L., Barcelona, Spain

[21] Appl. No.: 08/997,635

[22] Filed: Dec. 23, 1997

Related U.S. Application Data

[63] Continuation of application No. 08/535,125, filed as application No. PCT/ES95/00017, Feb. 6, 1995, abandoned.

[30] Foreign Application Priority Data

Feb. 8, 1994 [ES] Spain ...................................... 9400217

[51] Int. Cl.⁶ .................................................... A61K 31/05
[52] U.S. Cl. ............................................................. 514/737
[58] Field of Search ............................................... 514/737

[56] References Cited

U.S. PATENT DOCUMENTS 4,677,124  6/1987  Roquet-Jalmar ........................ 514/737

*Primary Examiner*—William R. A. Jarvis
*Attorney, Agent, or Firm*—Michael J. Striker

[57] ABSTRACT

The method of treating a leukotriene-mediated disease which is treatable by inhibition of 5-lipoxygenase includes administering a therapeutically effective amount of 2,4,6-triiodophenol, or a pharmaceutically acceptable salt or solvate thereof, for 5-lipoxygenase inhibition, together with an adequate amount of pharmaceutically acceptable excipients, diluents or carriers to the patient suffering from the disease. The diseases treated advantageously include, among others, herpes and gastrointestinal, respiratory, skin and/or ocular inflammatory diseases.

17 Claims, 4 Drawing Sheets

(1) 20-(OH)-LTB4  (2 & 3) 6-TRANS-LTB4 ISOMERS  (4) LTB4
(5 & 6) 5,6-DIHETE ISOMERS  (7) 15-HETE  (8) 12-HETE  (9) 5-HETE (1) 20-(OH)-LTB4  (2 & 3) 6-TRANS-LTB4 ISOMERS  (4) LTB4
(5 & 6) 5,6-DIHETE ISOMERS  (7) 15-HETE  (8) 12-HETE  (9) 5-HETE

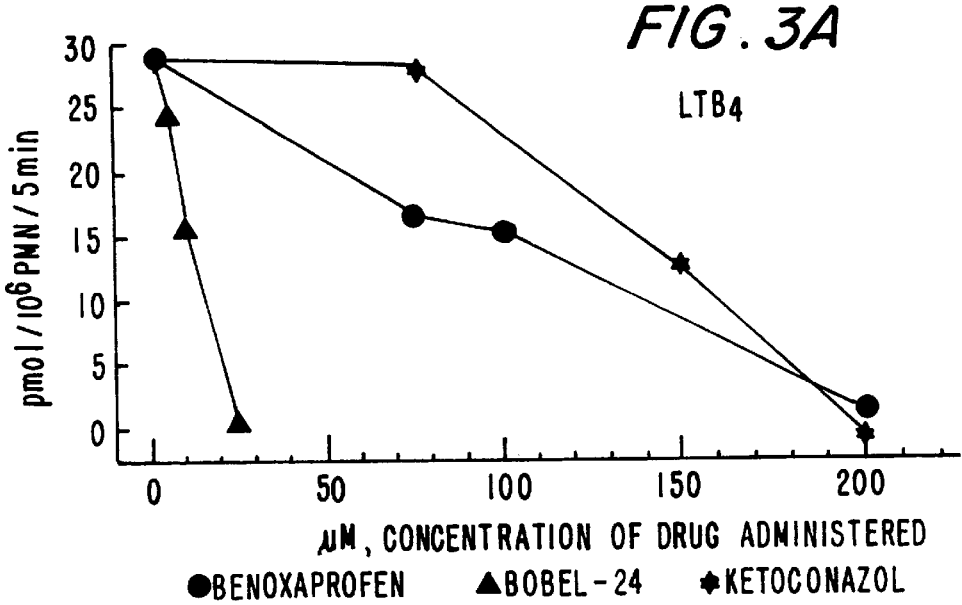
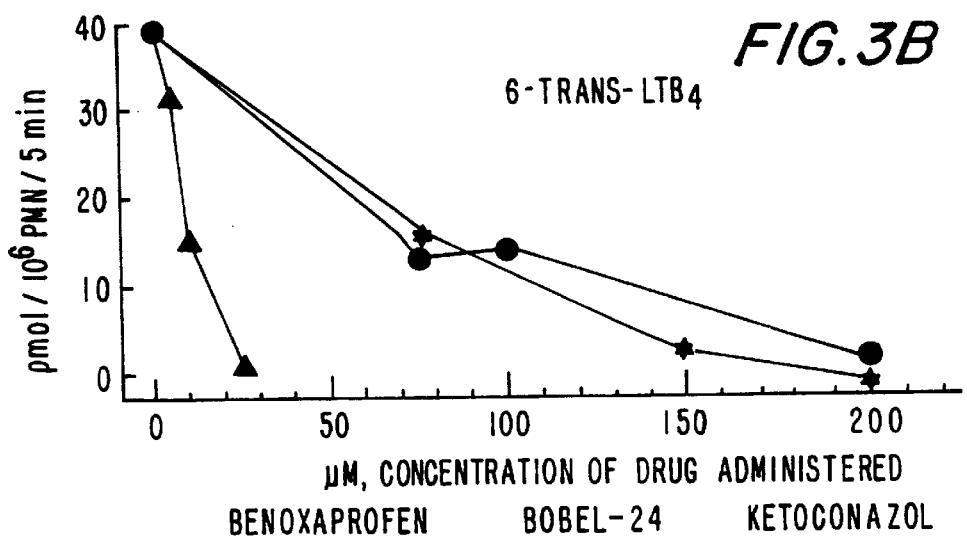
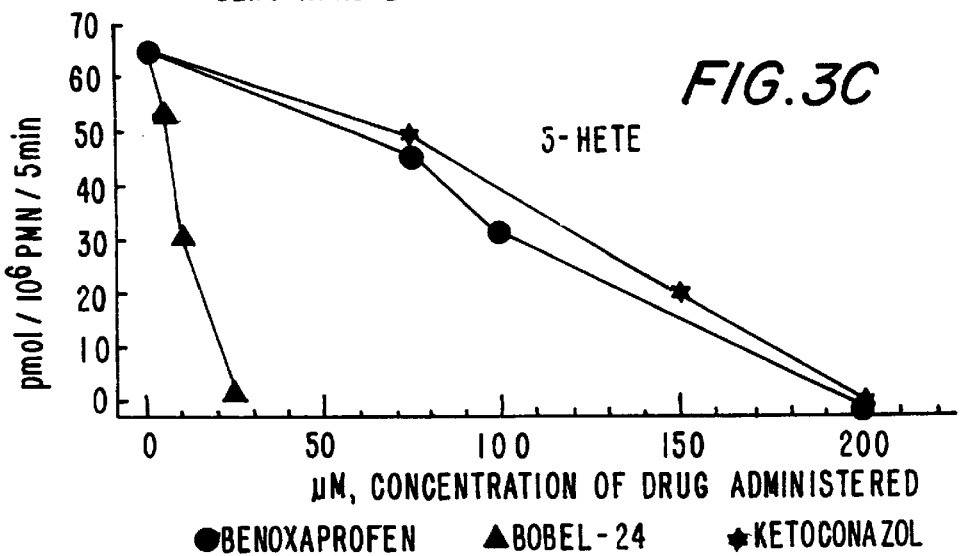

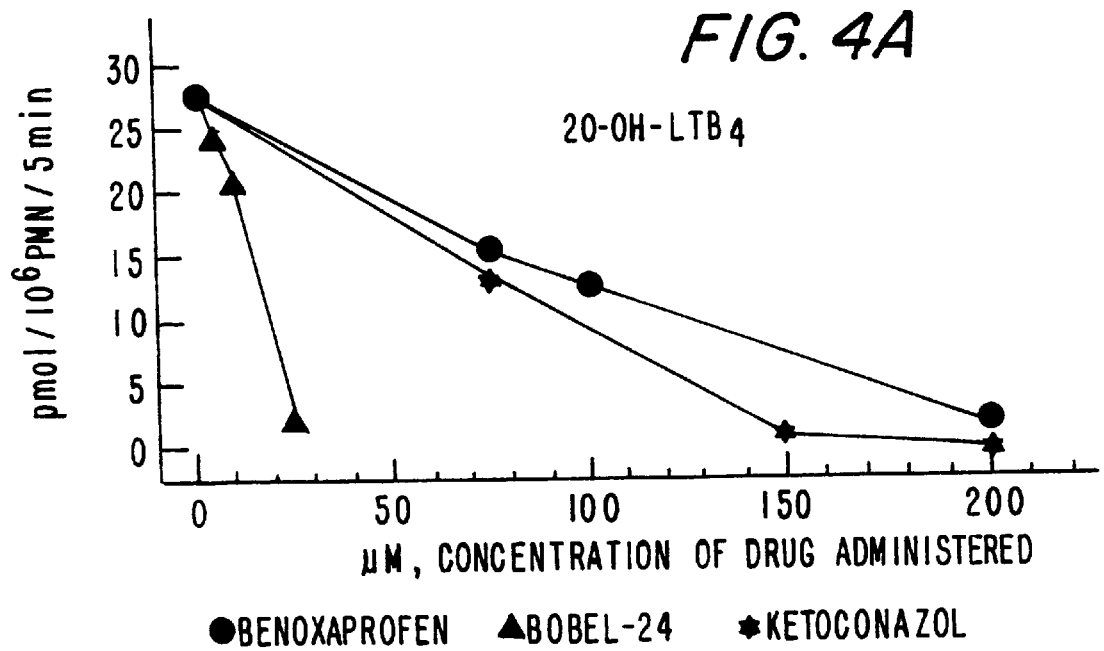
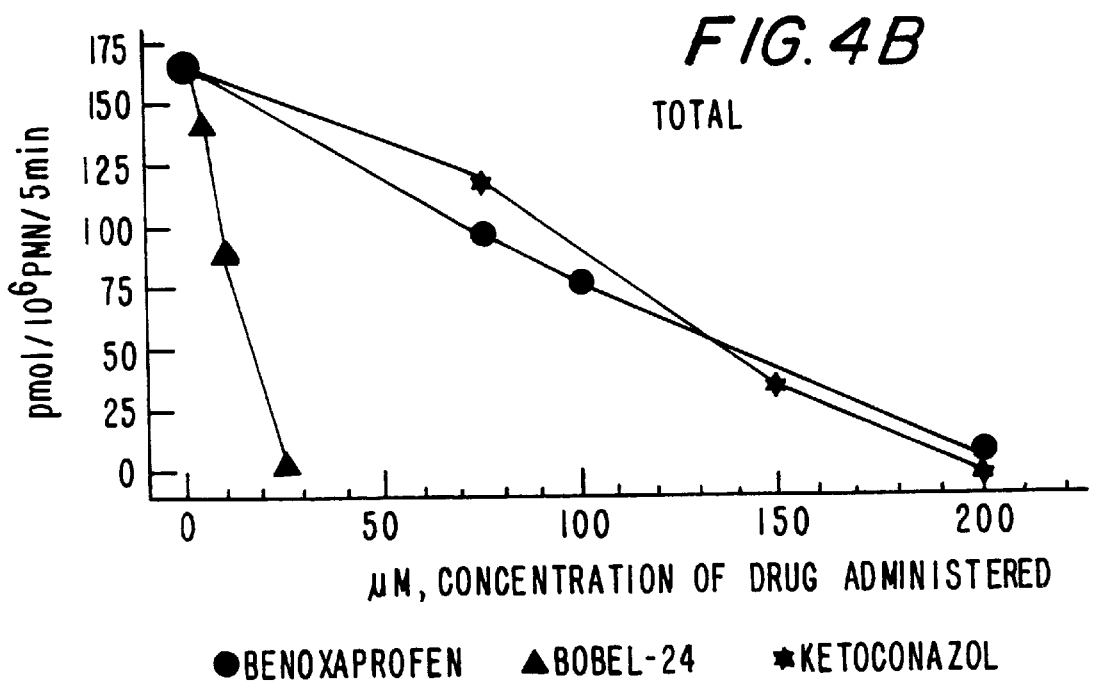

dideoxyphenol derivative of formula (I),

USE OF 2,4-DISTRIBUTED PHENOL DERIVATIVES AS 5-LIPOXYGENASE INHIBITORS

This application is a continuation of Ser. No. 08/535,125, filed Dec. 28, 1995, now abandoned, which is a 371 of PCT/E595/00017, filed Feb. 6, 1995.

BACKGROUND OF THE INVENTION

The present invention refers to the use in human and veterinary medicine of some 2,4-disubstituted phenol derivatives that, due to their surprisingly high 5-lipoxygenase inhibiting activity and to their low toxicity, are specially useful for the preparation of medicaments for the treatment of the numerous leukotriene-mediated diseases.

Cyclooxygenase inhibitors have been used in therapy for a long time, specially those referred to as non-steroidal antiinflammatory agents, such as aspirin, indomethacin, ibuprofen or piroxicam. It is known today that these products, by inhibiting the cyclooxygenase enzyme, prevent or make difficult the conversion of arachidonic acid into prostaglandins and thromboxanes. Unfortunately, the majority of these antiinflammatory agents present more or less severe adverse side effects, mostly of gastrointestinal type; therefore the research for new products with antiinflammatory activity still goes on.

Recently it has been found that 5-lipoxygenase (5-LO in the following) is an essential enzyme for the conversion of arachidonic acid into leukotrienes, and the later compounds and their metabolites play an important role in the genesis and development of numerous diseases. In the biomedical literature of the last years there are hundreds of publications which, with more or less evidence, associate leukotrienes with various diseases, including the following: musculoskeletal and inflammated joints diseases (rheumatoid arthritis, ostheoarthritis, juvenile arthritis, gout, arthrosis, discoespondilitis, bursitis, tendinitis, equine cauda . . . ); inflammatory diseases of the gastrointestinal tract (ulcerative colitis, Crohn disease, gastritis, chronic intestinal disease, rectitis, linphoplasmocitary enteritis . . . ); diseases involving inflammation of the respiratory tract (asthma, dyspnea, bronchitis, allergic rhinitis, adult respiratory distress syndrome . . . ); septic shock and shocks attributable to trauma, to ischemia of the gastrointestinal tract, to hemorrhage or to endotoxin; inflammatory diseases of the skin (psoriasis, eczema, dermatitis, leishmaniosis . . . ), diseases involving ocular inflammation (idiopathic keratitis, dry keratoconjuntivitis . . . ), as well as diseases attributable to allergies or hypersensitivity. The full knowledge of the mechanism of action of the leukotrienes and their metabolites is not yet fully known, and new therapeutic applications for 5-LO inhibitors are constantly being discovered. For example, as they substantially influence the organism, in some cases 5-LO inhibitors improve the defense mechanisms against the development or reoccurrence (metastasis) of cancerous tumors, or against the development of diseases involving microorganisms; therefore it is not surprising that the activity of 5-LO inhibitors is observed symptomatically in vivo but not in vitro.

The therapeutic interest in 5-LO inhibitors is quite high mainly because many of the diseases in which they are potentially useful still do not have satisfactory treatments. This is the case, for example, of asthma, psoriasis, ulcerative colitis, osteoarthritis or herpes, diseases which chronically affect a large part of the population and which still do not have a satisfactory therapy.

As a consequence of the previously stated, in the last years numerous pharmaceutical companies have been interested in the research and development of drugs with 5-LO inhibiting activity, as illustrated by dozens of patent applications published on the subject, and by the fact that more than 30 products with this activity appear in the databases on pharmaceutical products under development. However it is highly significant that, despite the high therapeutical interest of products with this activity, and despite the great efforts placed on their research and development, no satisfactory 5-LO inhibitor agent has reached the market yet, with the exception of ketaconozale and related products. This fact clearly indicates that there is a high difficulty involved in the development of such a product, what can be due to some of the following reasons: Some products, such as nordihydroguayaretic acid (NDGA), are very active but not enough specific (NDGA is a potent 5-LO inhibitor, but it is also inhibitor of all dioxygenases, and therefore cannot be used therapeutically). Other products, such as benoxaprofen and lonapalene, although they have been developed as 5-LO inhibitors, in practice they have turned out to be much too toxic (for this reason benoxaprofen was withdrawn, after having been commercialized). Others products, such as ketaconozale, although they have an acceptable toxical degree for an sporadic administration (in fact ketaconozale is being used as a fungicide), they are not acceptable for a chronic administration. Finally, other products have proved not to be active enough. Summarizing, there is no a good solution yet to the problem of having products that, showing a good 5-LO inhibiting activity, are little toxic and pharmaceutically viable.

The present invention provides a group of such products, all of which are derivatives of 2,4-disubstituted phenols, thus satisfactorily solving the above-mentioned problem. Several products of the present invention are chemically known in the literature, while others are completely new, although easy to prepare from available reactants. In either case, their 5-LO inhibiting activity has not been previously disclosed, and nothing in the previous art makes this activity obvious.

Patents EP 190.683, EP 235.575 and EP 372.409 mention 5-LO inhibiting activity for some 2,6-di-tert-butyl and 2,6-diphenyl phenol derivatives which are not included in the present invention. Patent EP 334.119 discloses as 5-LO inhibitors a group of phenols with a substituted vinyl radical at position 4, not included either in this invention. European patent application EP 147.892 mentions certain analgesic and antiinflammatory activity for a product which is included in the present invention, namely the 2,4,6-triiodophenol. But in this patent no specific leukotriene-mediated disease is mentioned (nothing is said, for instance, about asthma, psoriasis or ulcerative colitis); besides, the comparative tests disclosed in EP 147.892 were done against typical inhibitors of cyclooxygenase, such as indomethacin and aspirin. Therefore this document could suggest to an expert that 2,4,6-triiodophenol has some cyclooxygenase inhibiting activity (what is actually true and easily checked), this activity being typical of common analgesics and non-steroidal antiinflammatory agents. But nothing in that patent or in the common general knowledge teaches or makes obvious that 2,4,6-triiodophenol has one of the highest 5-Lo inhibiting activity ever disclosed. Such a teaching is part the present invention.

SUMMARY OF THE INVENTION

The present invention is based on use of a 2,4-disubstituted phenol derivative of formula (I),

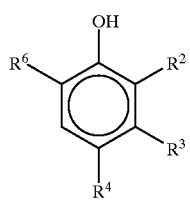

(I)

wherein:
R² is (C₁–C₄)-alkyl, (C₁–C₄)-acyl, CF₃, Cl, Br or I;
R³ is H, (C₁–C₄)-alkyl, (C₁–C₄)-acyl, (C₁–C₄)-alcoxyl, CF₃, F, Cl, Br, phenyl, OH, SH, NH₂ or amino mono- or disubstituted by (C₁–C₃)-alkyl;
R⁴ is (C₁–₄)-alkyl, (C₁–C₄)-acyl, CF₃, F, Cl, Br, I, carboxyl, (C₁–C₄)-alcoxycarbonyl, cyano, nitro or phenyl; and R⁶ is H, (C₁–C₄)-alkyl, (C₁–C₄)-acyl, CF₃, Cl, Br or I;

or the use of a pharmaceutically acceptable salt or solvate of said derivative, in the preparation of a 5-LO inhibitor medicament. Within these products, those where: R² is (C₁–C₄)-alkyl, CF₃, Cl, Br or I; R³ is H, (C₁–C₄)-alkyl, CF₃, F, Cl, Br, phenyl, OH, SH, NH₂ or dimethylamino; R⁴is (C₁–C₄)-alkyl, CF₃, F, Cl, Br, I, carboxyl, cyano, nitro or phenyl; and R⁶is H, (C₁–C₄)-alkyl, CF₃, Cl, Br or I, are preferred.

In a particular embodiment of the present invention, a 2,4-disubstituted phenol derivative of formula (I) where: R² is I; R³ is H, methyl, ethyl, isopropyl, tert-butyl, CF₃, F, Cl, Br, phenyl or OH; R⁴is methyl, ethyl, isopropyl, tert-butyl, CF₃, F, Cl, Br, I, carboxyl or phenyl; and R⁶ is H, isopropyl, tert-butyl, CF₃ or I, is preferred. Within these derivatives, those where: R³ is H, methyl, ethyl, isopropyl, tert-butyl, CF₃, Cl, Br or phenyl; R⁴ is isopropyl, tert-butyl, CF₃, Br, I, carboxyl or phenyl; and R⁶ is H, isopropyl, tert-butyl, CF₃ or I, are preferred. Even more preferred are those where: R³ is H; R⁴ is tert-butyl, CF₃, I or phenyl; and R⁶ is tert-butyl, CF₃ or I. The one where both R⁴ and R⁶ are I is the most preferred.

In another particular embodiment of the present invention, a 2,4-disubstituted phenol derivative of formula (I) where: R² is CF₃ or Br; R³ is H, methyl, ethyl, isopropyl, tert-butyl, CF₃, F, Cl, Br, phenyl or OH; R⁴ is methyl, ethyl, isopropyl, tert-butyl, CF₃, F, Cl, Br, I, carboxyl or phenyl; and R⁶ is H, isopropyl, tert-butyl, CF₃ or I, is preferred. Within these derivatives, those where: R³ is H, methyl, ethyl, isopropyl, tert-butyl, CF₃, Cl, Br or phenyl; R⁴ is isopropyl, tert-butyl, CF₃, Br, I, carboxyl or phenyl; and R⁶ is H, isopropyl, tert-butyl, CF₃ or I, are preferred. Even more preferred are those where: R³ is H; R⁴ is tert-butyl, CF₃, I or phenyl; and R⁶ is tert-butyl, CF₃ or I.

In another particular embodiment of the present invention, a 2,4-disubstituted phenol derivative of formula (I) where: R² is isopropyl or tert-butyl; R³ is H, methyl, ethyl, isopropyl, tert-butyl, CF₃, F, Cl, Br, phenyl or OH; R⁴ is methyl, ethyl, isopropyl, tert-butyl, CF₃, F, Cl, Br, I, carboxyl or phenyl; and R⁶ is H, isopropyl, tert-butyl, CF₃ or I, is preferred. Within these derivatives, those where: R³ is H, methyl, ethyl, isopropyl, tert-butyl, CF₃, Cl, Br or phenyl; R⁴ is isopropyl, tert-butyl, CF₃, Br, I, carboxyl or phenyl; and R⁶is H, isopropyl, tert-butyl, CF₃ or I, are preferred. Even more preferred are those where: R³ is H; R⁴ is tert-butyl, CF₃, I or phenyl; and R⁶ is tert-butyl, CF₃ or I.

In particular, derivatives in Table 1 are especially useful. This table indicates the internal names (company codes), the chemical names and the melting points (m.p.) of several 2,4-disubstituted phenol derivatives of formula (I) which have been prepared as examples.

TABLE 1

2,4-disubstituted phenol derivatives

| Code | Chemical name | m.p./° C. |
|---|---|---|
| Bobel-1 | 4-fluoro-2-iodophenol | oil |
| Bobel-2 | 4-tert-butyl-2-iodophenol | oil |
| Bobel-3 | 2-tert-butyl-4-iodophenol | oil |
| Bobel-4 | 2,6-diisopropyl-4-iodophenol | oil |
| Bobel-5 | 2,4-diiodophenol | 73 |
| Bobel-6 | 2-methyl-4,6-diiodophenol | 67 |
| Bobel-7 | 2-ethyl-4,6-diiodophenol | oil |
| Bobel-8 | 2-isopropyl-4,6-diiodophenol | oil |
| Bobel-9 | 2-tert-butyl-4,6-diiodofenol | 64–5 |
| Bobel-10 | 2-chloro-4,6-diiodophenol | 97–8 |
| Bobel-11 | 2-bromo-4,6-diiodophenol | 127 |
| Bobel-12 | 2-trifluoromethyl-4,6-diiodophenol | 77–8 |
| Bobel-13 | 4-methyl-2,6-diiodophenol | 63–5 |
| Bobel-14 | 4-isopropyl-2,6-diiodophenol | 37–9 |
| Bobel-15 | 4-tert-butyl-2,6-diiodophenol | 82–3 |
| Bobel-16 | 4-phenyl-2,6-diiodophenol | 86–9 |
| Bobel-17 | 4-fluoro-2,6-diiodophenol | 69–71 |
| Bobel-18 | 4-chloro-2,6-diiodophenol | oil |
| Bobel-19 | 4-bromo-2,6-diiodophenol | 129–30 |
| Bobel-20 | 4-trifluoromethyl-2,6-diiodophenol | 106–7 |
| Bobel-21 | 3-trifluoromethyl-2,6-diiodophenol | 79–81 |
| Bobel-22 | 4-nitro-2,6-diiodophenol | oil |
| Bobel-23 | 3-tert-butyl-2,4-diiodophenol | 85–8 |
| Bobel-24 | 2,4,6-triiodophenol | 157 |
| Bobel-25 | 3-methyl-2,4-6-triiodophenol | 122 |
| Bobel-26 | 3-ethyl-2,4,6-triiodophenol | 121–3 |
| Bobel-27 | 3-isopropyl-2,4-6-triiodophenol | 55–7 |
| Bobel-28 | 3-phenyl-2,4,6-triiodophenol | 123–5 |
| Bobel-29 | 3-fluoro-2,4,6-triiodophenol | 143 (d) |
| Bobel-30 | 3-chloro-2,4,6-triiodophenol | 137–9 |
| Bobel-31 | 3-bromo-2,4,6-triiodophenol | 155 (d) |
| Bobel-32 | 3-trifluoromethyl-2,4,6-triiodophenol | 65–6 |
| Bobel-33 | 3-hydroxy-2,4,6-triiodophenol | 145 (d) |
| Bobel-34 | 4-hidroxy-3,5-diiodobenzonitrile | oil |
| Bobel-35 | 2,4,6-tri-tert-butylphenol | oil |
| Bobel-36 | 4-hidroxy-3,5-diiodobenzoic acid | oil |

Table 2 shows the different values for the radicals of the products in Table 1 and indicates whether they are new or known. When known, it gives their respective Chemical Abstracts Service (CAS) Registry Numbers (RN), or alternatively their CA references (volume and abstracts number).

TABLE 2

Chemical Abstracts identification of the example products with formula (I)

| Name | R² | R³ | R⁴ | R⁶ | RN or CAS reference |
|---|---|---|---|---|---|
| Bobel-1 | I | H | F | H | RN = [2713-29-3] |
| Bobel-2 | I | H | t-Bu | H | RN = [38941-98-9] |
| Bobel-3 | t-Bu | H | I | H | RN = [60803-25-0] |
| Bobel-4 | i-Pr | H | I | i-Pr | New product |
| Bobel-5 | I | H | I | H | CA 24:5289 |
| Bobel-6 | Me | H | I | I | RN = [4186-52-1] |
| Bobel-7 | Et | H | I | I | New product |
| Bobel-8 | i-Pr | H | I | I | RN = [127502-66-3] |
| Bobel-9 | t-Bu | H | I | I | RN = [60803-26-1] |
| Bobel-10 | Cl | H | I | I | RN = [15459-49-1] |
| Bobel-11 | Br | H | I | I | RN = [89466-01-3] |
| Bobel-12 | CF3 | H | I | I | RN = [61494-84-6] |
| Bobel-13 | I | H | Me | I | RN = [2432-18-0] |
| Bobel-14 | I | H | i-Pr | I | RN = [2432-19-1] |
| Bobel-15 | I | H | t-Bu | I | RN = [75908-75-7] |
| Bobel-16 | I | H | Ph | I | CA 55:5845d |
| Bobel-17 | I | H | F | I | RN = [392-72-3] |
| Bobel-18 | I | H | Cl | I | RN = [15459-50-4] |

TABLE 2-continued

Chemical Abstracts identification of the example
products with formula (I)

| Name | $R^2$ | $R^3$ | $R^4$ | $R^6$ | RN or CAS reference |
|---|---|---|---|---|---|
| Bobel-19 | I | H | Br | I | RN = [15459-51-5] |
| Bobel-20 | I | H | CF3 | I | New product |
| Bobel-21 | I | CF3 | H | I | New product |
| Bobel-22 | I | H | NO2 | I | RN = [305-85-1] |
| Bobel-23 | I | t-Bu | I | H | New product |
| Bobel-24 | I | H | I | I | RN = [609-23-4] |
| Bobel-25 | I | Me | I | I | RN = [2109-12-8] |
| Bobel-26 | I | Et | I | I | RN = [124311-20-2] |
| Bobel-27 | I | i-Pr | I | I | New product |
| Bobel-28 | I | Ph | I | I | RN = [91353-81-0] |
| Bobel-29 | I | F | I | I | RN = [444-07-5] |
| Bobel-30 | I | Cl | I | I | RN = [89465-75-8] |
| Bobel-31 | I | Br | I | I | RN = [124311-19-9] |
| Bobel-32 | I | CF3 | I | I | New product |
| Bobel-33 | I | OH | I | I | RN = [19403-92-0] |
| Bobel-34 | I | H | CN | I | RN = [1689-83-4] |
| Bobel-35 | t-Bu | H | t-Bu | t-Bu | RN = [732-26-3] |
| Bobel-36 | I | H | COOH | I | RN = [618-76-8] |

Preparation of the the iodinated products of Table 1 which are not described in the literature is done through the iodination method published in Tetrahedron 1978, pp. 1577–9, as illustrated in Example 8.

Some of the products of formula (I) present stereoisomers. The use as 5-LO inhibitors of these isomers, separately or mixed, is also subject matter of the present invention.

The present invention also provides, as new and especially useful, products: 4-trifluoromethyl-2,6-diiodophenol (Bobel-20), and 2,6-diisopropyl-4-iodophenol (Bobel-4), as well as their pharmaceutically acceptable salts, their solvates and their compositions with pharmaceutically acceptable excipients. The most significative bands in IR spectroscopy of these new products are given (expressed in $cm^{-1}$).

Bobel-2: 3495, 3032, 2965, 1595, 1490, 1265, 1180, 875, 820, 695.

Bobel-3: 3540, 2955, 2870, 1700, 1490, 1305, 805.

Bobel-4: 3570, 2965, 1590, 1465, 1300, 1195, 872.

Bobel-12: 3445, 3080, 1590, 1455, 1305, 1150, 1130, 875, 685, 660.

Bobel-16: 3470, 3060, 3030, 1535, 1455, 1280, 1150, 875, 760, 705.

Bobel-20: 3450, 3090, 1595, 1465, 1405, 1315, 1120, 1094, 890, 715.

As 5-LO inhibitors, products of formula (I), or their pharmaceutically acceptable salts or solvates, are useful for the preparation of medicaments for the treatment of leukotriene-mediated diseases, with the preferences previously stated.

The present invention provides medicaments to treat the group of articular or musculoskeletal inflammatory diseases mediated by leukotrienes, such as: rheumatoid arthritis, ostheoarthritis, espondolitis, juvenile arthritis, gout, arthrosis, bursitis, tendonitis or equine cauda. In Example 2 there are illustrations of some treatments of this type.

The present invention also provides medicaments for the treatment of the group of gastrointestinal diseases mediated by leukotrienes, such as chronic intestinal pathologies, inflammatory bowel disease, Crohn disease or gastritis. In Example 5 there are illustrations of some treatments of this type.

Medicaments provided by the present invention are also useful for the treatment of inflammatory respiratory diseases mediated by leukotrienes, such as asthma, dyspnea, bronchitis, allergic rhinitis or adult respiratory distress syndrome. Example 3 illustrates some treatments of this type.

The present invention also provides medicaments for the treatment of septic shock or any shock attributable to trauma, to ischemia of the gastrointestinal tract, to hemorrhage or to endotoxin; as well as diseases involving allergies or hypersensibility attributable to leukotrienes.

Medicaments provided by the present invention are also useful for the treatment of diseases which belong to the group of inflammatory diseases involving skin, such as psoriasis, eczema, dermatitis or leishmanosis. Example 4 illustrates some treatments of this type.

Medicaments provided by the present invention are also helpful for the treatment of inflammatory ocular diseases, such as idiopathic or dry keratoconjutivitis.

Surprisingly, medicaments provided by the present invention are also useful for the in vivo eradication of symptoms of the group of diseases known as herpes, particularly herpes simplex and herpes zoster. Example 6 illustrates some treatments of this type.

As some other 5-LO inhibitors, the products of the present invention are also useful for the preparation of medicaments against cancerous metastasis.

5-Lipoxygenase (5-LO) is an enzyme expressed exclusively in myeloid white blood cells. It is a cytosolic enzyme, and whenever the cell is activated through an agent which causes a cytosolic $Ca^{2+}$ pulse it translocates coupling with a protein termed Five Lipoxygenase Activating Protein (FLAP). The role of this coupling in the activation of 5-LO remains unknown. However it is well known that 5-LO catalyses the first step in the biosynthesis of leukotrienes from arachidonic acid (AA), as schematically shown in FIG. 1. The first reaction that 5-LO catalyses is the conversion of AA into 5(S)-hydroperoxy-(E,Z,Z,Z)-6,9,11,14-eicosatetranoic acid (5-HPETE). By 5-LO catalysis, this hydroperoxide is transformed into an unstable epoxide, named leukotriene $A_4$ ($LTA_4$). Part of HPETE is reduced to the corresponding hydroxide, 5-HETE, through the action of a peroxidase. $LTA_4$ is the precursor of the transformations which lead to the formation of the rest of the leukotrienes. Thus, given that there are no alternative routes for the synthesis of leukotrienes, inhibition of 5-LO leads to the blockage of the biosynthesis of 5-HETE and of all leukotrienes.

As depicted in FIG. 1, it is known that, by enzymatic hydrolysis, $LTA_4$ is converted into leukotriene $B_4$ ($LTB_4$), what occurs in polymorphonuclears and other types of cells. Other reactions lead to the formation of the so-called peptidoleukotrienes. But, using suspensions of polymorphonuclears and low concentrations of AA (as in the examples of the present invention), the formation of this peptidoleukotrienes is rarely observed, $LTB_4$ and its isomers being the leukotrienes predominantly formed. It is known that in human polymorphonuclears $LTB_4$ is ω-oxidized, giving rise to 20-(OH)-$LTB_4$. $LTA_4$ also suffers non-enzymatic transformations giving rise to more stable products. Under the conditions of the examples the main products are those depicted in FIG. 1 (with their usual abbreviations), namely, the two 6-trans-$LTB_4$ acids and the two 5,6-DiHETE acids.

In order to show the 5-LO inhibiting activity of the products of the present invention, a specific test based on human polymorphonuclear leukocytes is chosen. In order to compare the present invention with its prior art, comparative test are carried out with Bobel-24 (one of the most active products tested in the invention) and the two drugs which are probably the closest to being used as 5-LO inhibitors: benoxaprofen and ketoconazole. The results show that the 5-LO inhibiting activity of the products of the present invention is an order of magnitude higher that the one of the two reference drugs. $IC_{50}$ values (micromolar concentration of the drug that results in a 50% inhibition of the AA transformed by 5-LO) are the following: $IC_{50}$=10 for Bobel-24, $IC_{50}$=92 for benoxaprofen, and $IC_{50}$=102 for ketaconozale. This means that, to obtain a given inhibition, the required concentration of Bobel-24 is approximately one tenth of the required concentration of benoxaprofen or ketaconozale, what is very surprising. Actually, the 5-LO inhibiting activity of Bobel-24 is one of the highest ever disclosed. Verification that this spectacular result is not an experimental artifact is done by checking that the liberation of lactatedehydrogenase (LDH) into the medium cannot be attributed to cellular lysis, but has to be directly attributed to the 5-LO inhibiting activity of Bobel-24.

For the use in therapy of the products of the present invention, their surprisingly low toxicity is crucial. In the case of Bobel-24, toxicity is negligible, as the following results show: Its acute toxicity in Sprague-Dawley rats is of $LD_{50}$=1.5 g/kg p.o.; acute toxicity in dogs is not observed after 28 days at doses of 200, 300, 400, 1000 and 2000 mg/kg (the later being the maximum administrable dose in practice); chronic toxicity in rats at a dose of 350 mg/kg.day is not observed after 6 months, neither at a hematological, biochemical, or anatomy-pathological level. No mutagenic activity of Bobel-24 is observed in any of the four bacterial strains tested.

The 5-LO inhibiting activity of some 2,4-disubstituted phenol derivatives of formula (I) has been determined through tests analogous to the one in Example 1. Results are shown in Table 3, expressed as percentage of inhibition at the minimum concentration (25 μM), some products showing 100% inhibition. It is observed in the table that, within experimental error, several products of formula (I) show activities of virtually 100%. The 2,4-disubstitution in the phenolic ring turns out to be a structural characteristic crucial for the presence of the 5-LO inhibiting activity. This has been observed in some control tests, e.g., in those carried out with the products of monoiodination of the phenol (i.e. 2-, 3- and 4-iodophenol) which show negligible activity.

TABLE 3

5-LO inhibitory activity of some of the 2,4-disubstituted phenol derivatives, ordered, and expressed as the approximate inhibition percentage at 25 μM concentration.

| Name | Chemical name | Activity (%) |
| --- | --- | --- |
| Bobel-20 | 4-trifluoromethyl-2,6-diiodophenol | 100 |
| Bobel-24 | 2,4,6-triiodophenol | 100 |
| Bobel-29 | 3-phenyl-2,4,6-triiodophenol | 100 |
| Bobel-12 | 2-trifluoromethyl-4,6-diiodophenol | 97 |
| Bobel-16 | 4-phenyl-2,4-diibdophenol | 97 |
| Bobel-25 | 3-methyl-2,4,6-triiodophenol | 97 |
| Bobel-3 | 2-tert-butyl-4-iodophenol | 96 |
| Bobel-8 | 2-isopropyl-4,6-diiodophenol | 95 |
| Bobel-4 | 2,6-diisopropyl-4-iodophenol | 94 |
| Bobel-26 | 3-ethyl-2,4,6-triiodophenol | 94 |
| Bobel-30 | 3-chloro-2,4,6-triiodophenol | 90 |
| Bobel-11 | 2-bromo-4,6-diiodophenol | 88 |
| Bobel-9 | 2-tert-butyl-4,6-diiodophenol | 87 |
| Bobel-14 | 4-isopropyl-2,6-diiodophenol | 85 |
| Bobel-15 | 4-tert-butyl-2,6-diiodophenol | 85 |
| Bobel-2 | 4-tert-butyl-2-iodophenol | 80 |
| Bobel-18 | 4-chloro-2,6-diiodophenol | 80 |
| Bobel-7 | 2-ethyl-4,6-diiodophenol | 74 |
| Bobel-10 | 2-chloro-4,6-diiodophenol | 73 |

The 2,4-disubstituted phenol derivatives of the present invention are anti-herpetic agents in vivo, since they eliminate the symptoms of patients suffering from different types of herpes simplex (genital herpes, herpes of mouth and lips, recurrent herpes), and of patients suffering from herpes zoster. There is no relapse after leaving the treatment. The products are active both intramuscularly and topically, the first via being preferred. In this case the mechanism of action of the products is unknown, although it is almost sure that is due to inhibition of 5-LO, since the products are inactive in vitro.

The 2,4-disubstituted phenol derivatives or their pharmaceutically acceptable salts, whose use is subject matter of the present invention, when conveniently associated with known additives and excipients, can be administrated orally, parenterally or topically; and in the form of injections, tablets, capsules, syrups, lotions, shampoos, creams, suppositories, eye-drops, etc. In Examples 9–12 several of these formulations are illustrated.

From what is here disclosed, it is evident that the use of the products of the present invention, subject matter of the same, constitute a great advance in the treatment of leukotriene-mediated diseases, with important advantages over the use of products previously known in the art.

BRIEF DESCRIPTION OF THE DRAWINGS

The objects, features and advantages of the invention will now be illustrated in more detail with the aid of the following description of the preferred embodiments, with reference to the accompanying figures in which:

FIG. 3 is a graphical illustration of respective concentrations of different products derived from 5-LO activity, in studies using Bobel-24, benoxaprofen and ketoconazole; and FIG. 4 is another graphical illustration of respective concentrations of different products derived from 5-LO activity, in studies using Bobel-24, benoxaprofen and ketoconazole.

EXAMPLES

Example 1

Figure 1:
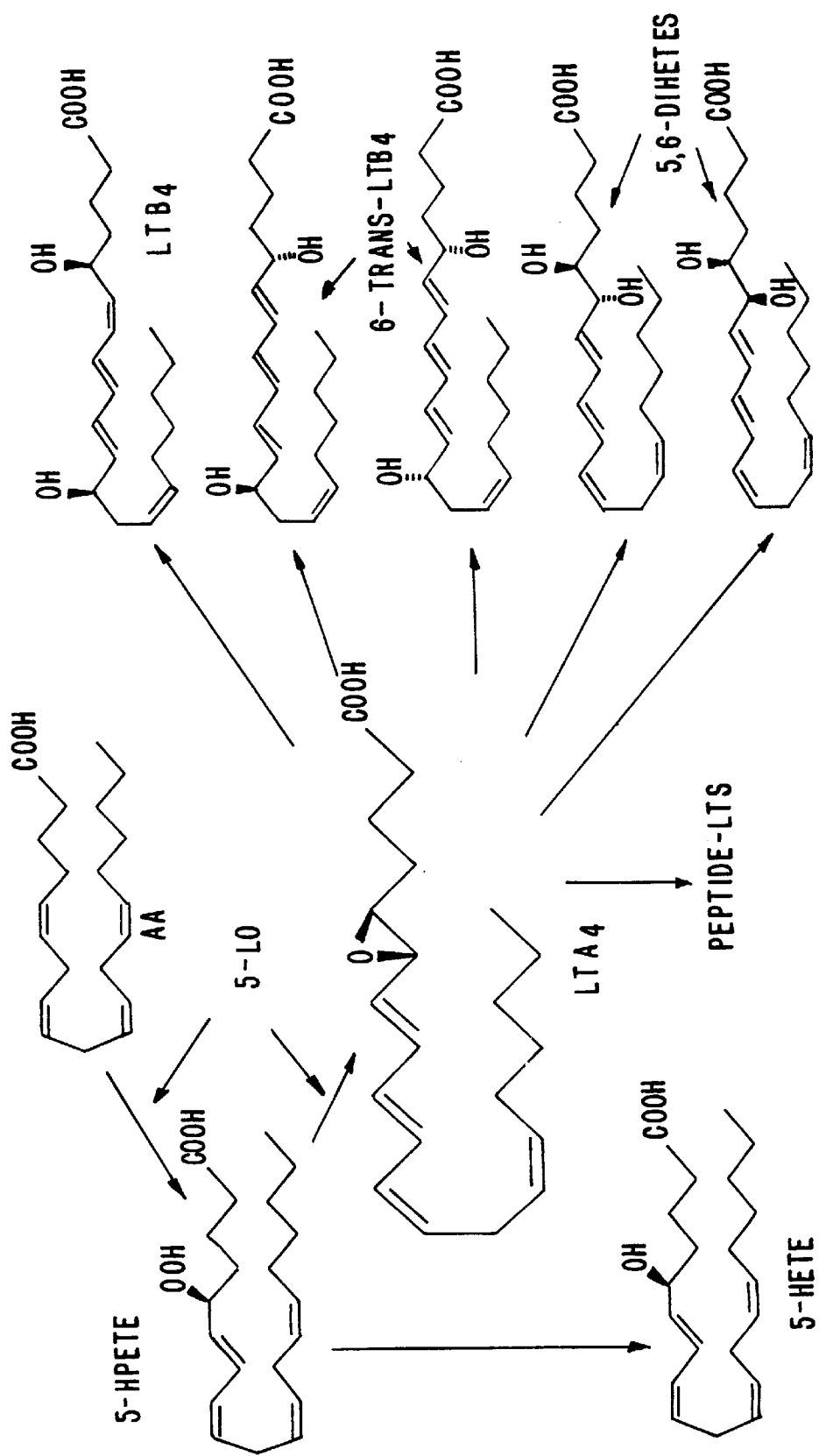
FIG. 1 shows a known mechanism for biosynthesis of leukotrienes from arachidonic acid as well as the manner in which 5-LO participates in this mechanism.

5-LO Inhibiting Activity in Polymorphonuclear Leukocytes
a) Preparation of the Suspensions of Polymorphonuclear Leukocytes Blood was obtained from donors which had not received medication during the ten days previous to the extraction. The blood was treated with an anticoagulant (ACD-A) and was centrifuged at 200 g during 12 min at room temperature, separating the supernatant. A solution of Dextran T-500 in physiological serum was added to the pellet, in order to obtain a final concentration of 0.6% w/v, and was allowed to sediment during 40 min. The supernatant was centrifuged at 180 g during 10 min at room temperature. The pellet was resuspended in 5 ml of Hank's buffer, pH 7.4. After the addition of 3 ml of Lymphoprep, the suspension was centrifuged at 450 g during 30 min, and the layers of supernatant were discarded. The next step was the lysis of the erythrocytes present by adding 2 ml of a saline solution. The resulting volume was adjusted to 10 ml with Hank's buffer, pH 7.4. The solution was centrifuged during 10 min at 180 g; the supernatant was discarded and the resulting pellet was resuspended in 1–2 ml of Hank's buffer, pH 7.4. The cellular density was determined using a haemocytometer using the procedure of microcollection Unopette to determine the levels of platelet contamination. Cellular density was adjusted to $2\times10^7$ cells/ml with Hank's buffer, pH 7.4 and $CaCl_2$ was added to a final concentration of 1.5 mM.

b) Eicosanoid Formation from 5-lipoxygenase (5-LO) Activity

The necessary amounts of the drugs to be used were dissolved in DMSO (control, benoxaprofen, ketaconozale, Bobel) in order to obtain the final concentrations shown in the results tables. Aliquots (0.5 ml) of the polymorphonuclear leukocytes suspensions, obtained as described in part (a), were incubated during 5 min at 37° C. in the absence (control) and in the presence of three different concentrations of each drug. Afterwards an ethanol solution of [$^{14}C$]-arachidonic acid and A23187 ionophore was added to obtain a final concentration of 10 and 5 $\mu$M, respectively. After 5 min of incubation the reaction was stopped by addition of 0.5 ml of ice-cold ethanol. Samples were centrifuged during 2 min at 1500 g, and the supernatants were kept at −80° C. until analyzed. Controls were carried out using the polymorphonuclear leukocyte suspensions aliquots in the presence of the solvent (DMSO) only.

c) Conditions for the Analysis of the Eicosanoids Formed

The analysis of the products from the transformation of arachidonic acid through the action of the lipoxygenase (these products being the eicosanoids) was carried out using high pressure liquid chromatography (HPLC), in a reverse phase column (Ultrasphere-ODS, Beckman), injecting 500 $\mu$l of the supernatants obtained from the incubations. Elution was carried out using an isocratic mix of mathanol:water:triethylamine:trifluoroacetic acid, 75:25:0.05:0.10, with a flux of 1 ml/min. Detection was carried out with a radioactivity detector with a liquid scintillation cell on-line coupled with the column.

d) Inhibition Results

Figure 2A:
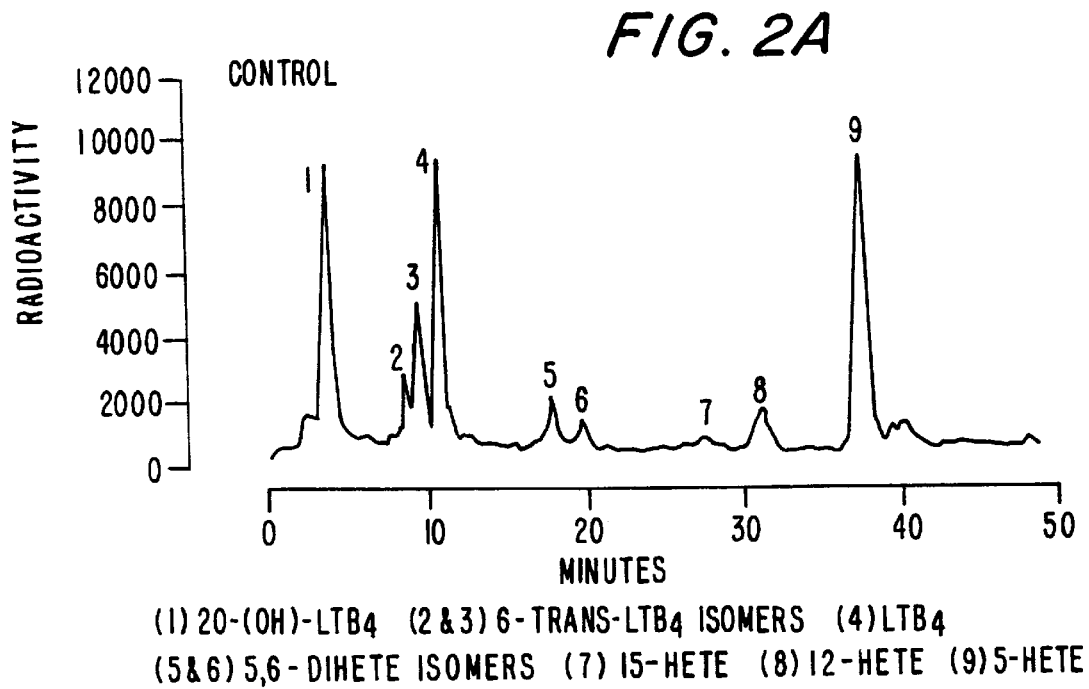
FIG. 2 are respective chromatograms from a control and sample treated with Bobel-24 at a concentration of 25 μm.
Figure 2B:
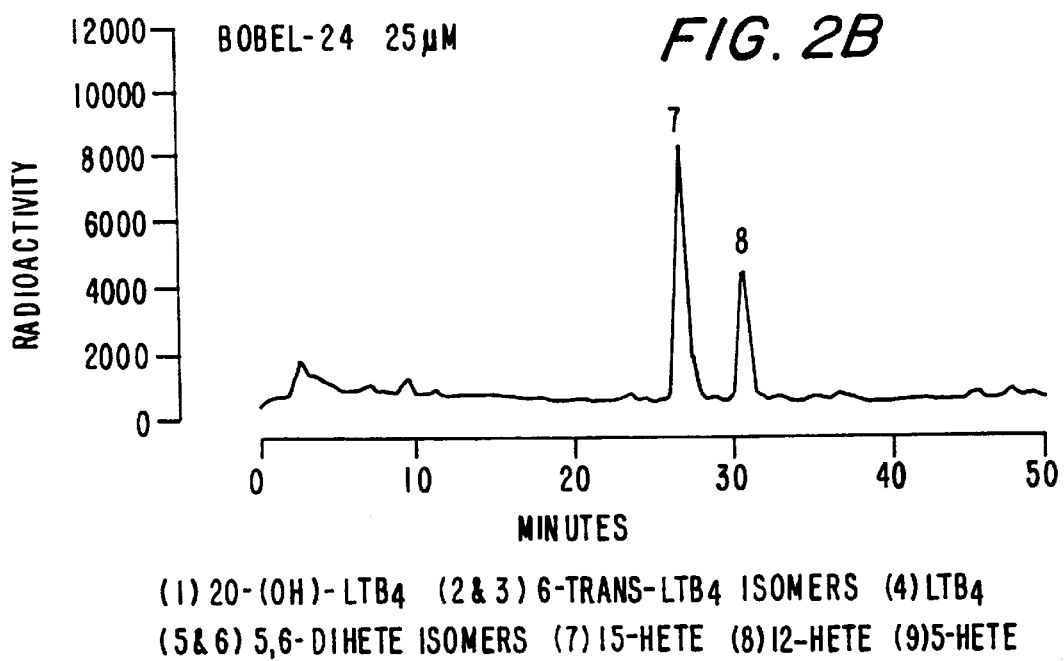

FIG. 2 depicts two typical chromatograms obtained from a control and a sample treated with Bobel-24, at a concentration of 25 $\mu$M; the initial concentration of arachidonic acid was of 10 $\mu$M. As shown in the chromatogram, and according with what is known, polymorphonuclear biosynthesis produced $LTB_4$ (peak 4), the two 6-trans-$LTB_4$ isomers (peaks 2 and 3), 5-HETE (peak 9) and 20-(OH)-$LTB_4$ (peak 1). The chromatogram of the sample treated with Bobel-24 showed the practically complete disappearance of the products derived from 5-LO biosynthesis, together with an increment in 15-HETE and 12-HETE (due to contaminating platelets). Thus it showed a clear inhibition of 5-LO activity. Integration of the corresponding peaks allowed the measurement of the concentration of each product, and this clearly indicated the dependence on the nature and concentration of the drug used.

FIGS. 3 and 4 show the values of the concentrations of the different products derived from 5-LO activity, in studies using Bobel-24 and other two known drugs (benoxaprofen and ketoconozale), with different concentrations of the drugs. The concentration of the five biosynthesis products analyzed ($LTB_4$, 6-trans-$LTB_4$, 5-HETE, 20-OH-$LTB_4$ and 5-HETE) decreased in approximately linear with the concentration of the drug used. However, the gradients were greater in the case of Bobel-24 than with the other two. This means a surprisingly high 5-LO inhibiting activity with Bobel-24, much greater than with the other two. Quantitatively this difference could be expressed through the $IC_{50}$ values (micromolar concentration of the drug which inhibits 50% of the AA converted by 5-LO), calculated adding all the corresponding peaks and obtaining the average of five different peaks. The following values were obtained: $IC_{50}$= 10±2 for Bobel-24, $IC_{50}$=92±19 for benoxaprofen and $IC_{50}$= 102±24 for ketaconozale. Therefore in order to obtain a given inhibition, it is enough with a concentration ten times smaller of Bobel-24 than of benoxaprofen or ketaconozale.

Example 2.
Activity in Cases of Articular or Muscleskeletal Diseases

A total of twenty dogs from different breeds and had been diagnosed rheumatoid arthritis, hip dysplasia, equine cauda, deforming spondolitis or coxarthrosis with possible Legg-Perthes-Calve, were treated with oral doses of Bobel-24 between 1 and 3 mg/kg.day, obtaining very good response within 1 or 2 weeks.

Seven young horses with bursitis were administrated 15 mg/day of Bobel-24 via intraarticular infiltration and a reduction in the inflammation was obtained.

Twenty five horses suffering from tendonitis, with claudication of the corresponding tendon, were treated with 15 mg/day via intraarticular infiltration of Bobel-24. In 17 cases the process was totally reduced in 15 days. In the rest of the cases the claudication disappeared within the same period of time, but an inflammatory ring persisted around the tendon.

Example 3
Activity in Cases of Respiratory Diseases

The administration of 5 mg/day of Bobel-24 to cats suffering from feline asthma, in the form of a sticky and sweet cream applied to the leg of the animal, so that it would ingest the drug whenever it licked it's leg, gave satisfactory results in many cases.

Eleven race horses manifesting dyspnea of variable degree, accompanied of great sensibility in the movements and, in the majority of the cases respiratory anxiety, coughs and mucous-purulent nasal flux, were treated with an intravenous dose of Bobel-24 of 50 mg/day during one week. The improvement was quite high, with regression of all the symptoms which disappeared within 9 days. None of the horses suffered relapse, and they reincorporated to training after 21 days, without any sequel.

Example 4
Activity in Cases of Skin Inflammatory Diseases

A total of 15 dogs (Cockers) suffering from seborrheic dermatitis in phase I or II were treated with doses of 1 mg/kg.day p.o. of Bobel-24, and were simultaneously washed with a shampoo containing 2% of the same product. The results were spectacular, with practically a total disappearance of the dermatitis. Besides, five German Shepherds suffering from leishmanosis were also treated, with similar results.

Example 5
Activity in Cases of Gastrointestinal Diseases

A total of ten dogs diagnosed chronic intestinal pathology, chronic lymphoplasmocitary enteritis (diagnosed through a biopsy and more than a year of evolution) and hemorrhagic cholitis, were treated with doses of 1–2 mg/kg.day of Bobel-24. The animals responded very positively in a short time (1–2 weeks).

Example 6
In Vivo Activity in Cases of Herpes Simplex

A total of 25 patients with symptoms of different herpes simplex (genital, buccal or reincident) were treated with 15 mg/day of Bobel-24, intramuscularly, during a month, with the following results: with the ten patients of genital herpes simplex, the results was excellent in 7 cases, good in 2 and regular in 1; of the twelve with buccal herpes simplex it was excellent in 9 cases, good in 2 and regular in 1; of the 3 with reincident herpes it was excellent in 2 of the cases and good in 1. Therefore there was a clear and generalized disappearance of the symptoms. The case of genital herpes which resulted "regular" was an obese and diabetic woman, and although there was an improvement there was also reincidency. Independently an test for antiviral activity in vitro resulted negative.

Example 7
In Vivo Activity in Cases of Herpes Zoster

A total of 21 patients with clear symptoms of herpes zoster were treated with 15 mg/day of Bobel-24, via intramuscular injection, during a month. The results concerning the disappearance of the symptoms were the following: excellent in 18 cases, good in 2 cases, and regular in 1 case.

Example 8
General Process for the Preparation of the Iodophenols

One part of the original non-iodinated phenol was dissolved in 15 parts of glacial acetic acid. Potassium iodide was added according to the stoichiometry of the reaction (1, 2 or 3 equivalents), shaking strongly and continuously. The solution temperature was lowered to 0° C., and the first portion of (3 parts in volume) of hydrogen peroxide 30% w/v in water, was started. The addition is carried out dropwise during approximately half an hour. The solution is allowed to reach room temperature. A second addition of hydrogen peroxide was done (1.5 volumes), at the same rate, keeping the solution temperature below 45° C. Shaking is maintained for 2 h, and a third addition is done, shaking for 30 minutes. When the color of iodine disappeared the reaction is finished.

If the product precipitates spontaneously from the medium, it is separated by filtration. If it does not, precipitated by the addition of water or, alternatively, water is added (30 parts in volume) and is extracted with dichloromethane. The crude solid or the organic extract is washed with an aqueous solution of 5% sodium bisulfite, and then with water. The organic extract is dried over magnesium sulfate; the solvent is eliminated under vacuum, and the solid or the resulting oil is dried. Sometimes the product contains products of different iodination degrees, which can be separated by silicagel chromatography, with hexane:diethyl ether, 5:1 as eluent.

Example 9
Preparation of Injectables

A thousand injectables containing each one 25 mg of Bobel-24 were prepared using 15 g Bobel-24, 20 g lysine, 35 g sodium chloride and 5000 ml water for injectables, and dosifying at 5 ml per injectable.

Example 10
Preparation of Capsules

Using magnesium estereate as the lubricant and lactose as the solvent, hard gelatin capsules (Shionogi Qualicaps, Japan) were prepared, with the following composition. 100 mg capsules: log of Bobel-24, 1 g of magnesium stearate, 16 g of lactose. 25 mg capsules: 2.5 g of Bobel-24, 1 g of magnesium stearate, 12.5 g of lactose. 10 mg capsules: 1.0 g of Bobel-24, 1 g of magnesium stearate, 13 g of lactose.

Example 11
Preparation of Shampoo

Due to the insolubility of Bobel-24 in aqueous medium, it was previously dissolved in a 50% solution of lysine. An anionic sulfonated detergent was used as foaming agent, containing 10–15% tegobetaine, 20–30% texapone N-40, and water. A 2% shampoo was prepared with the following composition: 2 g Bobel-24, 12 ml of 50% aqueous solution of lysine, 48 ml of water, 40 ml of the anionic sulfonated detergent.

Example 12
Preparation of Eye-drops

Bobel-24 was incorporated in a 50% solution of lysine. Sodium chloride in order to obtain an isotonic solution and EDTA as a chelating agent. Eye-drops (0.5%) were prepared with the following composition: 0.5 g of Bobel-24, 3 ml of a 50% solution of lysine, 10 ml EDTA, 0.5 g NaCl, and water to make up 100 ml.

Example 13
Clinical Trial on Canine Arthrosis

After the diagnosis, each animal was treated with Bobel capsules during 45 days, with a follow up every 15 days. Blood, synovial liquid and urine samples were taken at the beginning and at the end of the treatment in order to perform the following tests: Synovial liquid analysis (cytology, cytokines 1,6,8 and TNF); $LTB_4$; $LTC_4$; $PGE_2$; hematic count and leukocyte content; standard serum biochemistry; urine sediment; Rose-Wealer test; and radiology control. The methodology for clinical validation involved applying evaluating uniform parameters and classifying the results according to the following notations: (+++)=very good response, total recovery; (++)=good response, functionability recovery; (+)=moderate response, improvement; (−)= negative response or no apparent improvement. The results obtained are shown in Table 4.

TABLE 4

Evolution of the dogs after 45 days of treatment with 4 mg/kg day of Bobel-24 orally.

| Breed | Age/years | Diagnostic | Evolution |
| --- | --- | --- | --- |
| Mastif | 11 | Equine cuada | +++ |
| Doge | 3 | Spondolytis | +++ |
| Rottwailer | 1 | Arthrosis | +++ |
| Mongrel | 14 | Rotular arthrosis | ++ |
| German shepherd | 2 | Broken muscle | + |
| Mongrel | 13 | Equine cauda | +++ |
| German shepherd | 10 | Generalized arthrosis | ++ |
| German shepherd | 9 | Arthrosis | +++ |
| Poodle | 15 | Broken crossed ligament | + |
| Poodle | 11 | Degenerative arthrosis | +++ |

Example 14
Clinical Trial on Canine Arthritis

After the diagnosis each animal was treated with capsules of Bobel-24 during 15 days. Blood, synovial liquid and urine samples were taken at the beginning and at the end of the treatment in order to perform the same tests as in example 13, using the same notation for the clinical evolution. The results obtained are shown in Table 5.

TABLE 5

Evolution of the dogs after 15 days of treatment with 2 mg/kg day of Bobel-24, orally.

| Breed | Age/years | Diagnosis | Evolution |
| --- | --- | --- | --- |
| Mongrel | 1 | Osteochondritis | +++ |
| Mongrel | 8 | Arthritis | +++ |
| German shepherd | 6 | Arthritis | +++ |
| Rottwailer | 1 | Arthritis | +++ |

TABLE 5-continued

Evolution of the dogs after 15 days of treatment with 2 mg/kg day of Bobel-24, orally.

| Breed | Age/years | Diagnosis | Evolution |
|---|---|---|---|
| German shepherd | 2 | Knee instability | ++ |
| Mongrel | 7 | Arthritis | +++ |

Example 15
Clinical Trial on Canine Seborrheic Dermatitis

The animals had been diagnosed to suffer from seborrheic dermatitis, and the diagnosis was confirmed by a biopsy. The treatment consisted of a weekly bath with a 2% Bobel-24 shampoo and evaluation of the treatment after 15 days. The efficiency of the treatment was analyzed evaluating the following therapeutic symptoms; removal of scabs and scales, greasiness reduction, sheborrheic odor reduction, relieve of the pruritus, and antiinflammatory effect. Clinical evaluation is shown in Table 6, where the following notation is used: (+++)=very good response, clinically cured; (++)= good response, marked lowering in the clinical signs; (+)= moderate response, improvement; (−)=negative response or no apparent improvement. In view of the results the following conclusions were reached:

a) In patients with idiopathic seborrheic dermatitis the result was excellent, with an improvement similar to the one obtained with the oral therapy of corticoids. In this dermopathies it is not necessary to complement with topical therapy.

b) In secondary seborrheic dermatitis it is not necessary to supply, together with the Bobel-24 shampoo, the selected treatment for the primary pathology, due to the fact that the shampoo improves the aspect of the fur, but does not combat the ethiological agent responsible for the disease.

c) In all the animals tested, except in one affected with dermatophytosis, a lowering of the scabs, disappearance of the greasiness and the seborrheic odor, disappearance of the erithema and the pruritus was observed.

d) The treatment appears to be one of the topical treatments most effective, being remarkable the absence of secondary or adverse effects such as mucosal or skin irritation, and unpleasant smells.

TABLE 6

Evolution of dogs diagnosed seborrheic dermatitis, after 15 days of topical treatment with a weekly bath of Bobel-24 2% shampoo.

| Breed | Age/years | Etiology | Evolution |
|---|---|---|---|
| Poodle | 6 | allergic | ++ |
| Mongrel | 14 | allergic | + |
| Scotty T | 4 | dermatophytes | − |
| Cocker A | 13 | idiopathic | +++ |
| German shepherd | 10 | leishmania | + |
| Mongrel | 4 | demodex | ++ |
| Yorkshire | 7 | follicular cyst | ++ |
| Pekinese | 2 | pyoderma | ++ |
| Mongrel | 10 | allergic | + |
| Belgian shepherd | 10 | allergic | + |
| Pekinese | 11 | leishmania | ++ |
| German shepherd | 3 | leishmania | ++ |
| Schnauzer | 3 | dermatomycosis | ++ |
| Poodle | 9 | allergic | ++ |
| Scotty T | 4 | allergic to fleas | ++ |
| German shepherd | 1 | dermatomycosis | ++ |
| Cocker A | 9 | hypothyroidism | ++ |
| Cocker S | 8 | leishmaniosis | ++ |
| Mongrel | 5 | allergic | + |
| Cocker S | 15 | idiopathic | +++ |
| Cocker S | 12 | idiopathic | +++ |
| German shepherd | 10 | pyoderma | ++ |

We claim:

1. A method of treating a leukotriene-mediated disease in a patient, said patient being human or animal and said leukotriene-mediated disease being treatable by inhibition of 5-lipoxygenase, said method comprising the step of administering to said patient a therapeutically effective amount of 2,4,6-triiodophenol, or a pharmaceutically acceptable salt or solvate thereof, together with an adequate amount of pharmaceutically acceptable excipients, diluents or carriers, wherein said effective amount is sufficient for inhibition of said 5-lipoxygenase in said patient and wherein said disease is not a joint or musculoskeletal inflammatory disease.

2. The method as defined in claim 1, wherein the disease belongs to the group of gastrointestinal inflammatory diseases.

3. The method as defined in claim 2, wherein the disease is chronic intestinal pathology, ulcerative colitis, Crohn's disease, gastritis, rectitis or lymphoplasmacitarial enteritis.

4. The method as defined in claim 1, wherein the disease belongs to the group of respiratory inflammatory diseases.

5. The method as defined in claim 4, wherein the disease is asthma, dyspnea, bronchitis, allergic rhinitis or adult respiratory distress syndrome.

6. The method as defined in claim 1, wherein the disease is septic shock or shock attributable to trauma, to intestinal tract ischemia, to hemorrhage or to endotoxin.

7. The method as defined in claim 1, wherein the disease belongs to the group of skin inflammatory diseases.

8. The method as defined in claim 7, wherein the disease is psoriasis, eczema, dermatitis or leishmaniosis.

9. The method as defined in claim 1, wherein the disease belongs to the group of ocular inflammatory diseases.

10. The method as defined in claim 1, wherein the disease is idiopathic keratitis or dry keratoconjunctivitis.

11. The method as defined in claim 1, wherein the disease is herpes.

12. The method as defined in claim 11, wherein the herpes is simplex or zoster.

13. The method as defined in claim 1, wherein the disease is cancerous metastasis.

14. A method of treating herpex simplex or herpes zoster in a patient, said patient being human or animal, said method comprising the step of administering to said patient a therapeutically effective amount of 2,4,6-triiodophenol, or a pharmaceutically acceptable salt or solvate thereof, together with an adequate amount of pharmaceutically acceptable excipients, diluents or carriers, wherein said effective amount is sufficient for effective treatment of said herpex simplex or herpes zoster.

15. A method of treating asthma in a patient, said patient being human or animal, said method comprising the step of administering to said patient a therapeutically effective amount of 2,4,6-triiodophenol, or a pharmaceutically acceptable salt or solvate thereof, together with an adequate amount of pharmaceutically acceptable excipients, diluents or carriers, wherein said effective amount is sufficient for effective treatment of said asthma.

16. A method of treating ulcerative colitis or lymphoplasmacitarial enteritis in a patient, said patient being human or animal, said method comprising the step of administering to said patient a therapeutically effective amount of 2,4,6-triiodophenol, or a pharmaceutically acceptable salt or solvate thereof, together with an adequate amount of pharmaceutically acceptable excipients, diluents or carriers, wherein said effective amount is sufficient for effective treatment of said ulcerative colitis or lymphoplasmacitarial enteritis.

17. A method of treating dermatitis in a patient, said patient being human or animal, said method comprising the step of administering to said patient a therapeutically effective amount of 2,4,6-triiodophenol, or a pharmaceutically acceptable salt or solvate thereof, together with an adequate amount of pharmaceutically acceptable excipients, diluents or carriers, wherein said effective amount is sufficient for effective treatment of said dermatitis.

\* \* \* \* \*